(12) United States Patent
Lipp et al.

(10) Patent No.: US 9,387,169 B2
(45) Date of Patent: Jul. 12, 2016

(54) RAPAMYCIN POWDERS FOR PULMONARY DELIVERY

(71) Applicant: Civitas Therapeutics, Inc., Chelsea, MA (US)

(72) Inventors: Michael M. Lipp, Framingham, MA (US); Abhijit Kamerkar, Salem, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

(21) Appl. No.: 14/934,491

(22) Filed: Nov. 6, 2015

(65) Prior Publication Data

US 2016/0128936 A1    May 12, 2016

Related U.S. Application Data

(60) Provisional application No. 62/076,651, filed on Nov. 7, 2014.

(51) Int. Cl.
*A61K 9/00* (2006.01)
*A61K 31/436* (2006.01)

(52) U.S. Cl.
CPC ........... *A61K 9/0075* (2013.01); *A61K 31/436* (2013.01)

(58) Field of Classification Search
None
See application file for complete search history.

(56) References Cited

U.S. PATENT DOCUMENTS

| | | |
|---|---|---|
| 3,929,992 A | 12/1975 | Sehgal et al. |
| 5,080,899 A | 1/1992 | Sturm et al. |
| 5,635,161 A | 6/1997 | Adjei et al. |
| 5,855,913 A | 1/1999 | Hanes et al. |
| 5,874,064 A | 2/1999 | Edwards et al. |
| 5,985,309 A | 11/1999 | Edwards et al. |
| 5,989,591 A | 11/1999 | Nagi |
| 6,136,295 A | 10/2000 | Edwards et al. |
| RE37,053 E | 2/2001 | Hanes et al. |
| 6,254,854 B1 | 7/2001 | Edwards et al. |
| 6,258,823 B1 | 7/2001 | Holt et al. |
| 6,384,046 B1 | 5/2002 | Schuler et al. |
| 6,399,102 B1 | 6/2002 | Edwards et al. |
| 6,419,900 B2 | 7/2002 | Placke et al. |
| 6,419,901 B2 | 7/2002 | Placke et al. |
| 6,436,443 B2 | 8/2002 | Edwards et al. |
| 6,447,752 B2 | 9/2002 | Edwards et al. |
| 6,447,753 B2 | 9/2002 | Edwards et al. |
| 6,451,784 B1 | 9/2002 | Placke et al. |
| 6,503,480 B1 | 1/2003 | Edwards et al. |
| 6,635,283 B2 | 10/2003 | Edwards et al. |
| 6,652,837 B1 | 11/2003 | Edwards et al. |
| 6,732,732 B2 | 5/2004 | Edwards et al. |
| 6,740,310 B2 | 5/2004 | Edwards et al. |
| 6,766,799 B2 | 7/2004 | Edwards et al. |
| 6,793,912 B2 | 9/2004 | Pilkiewicz et al. |
| 6,848,197 B2 | 2/2005 | Chen et al. |
| 6,858,199 B1 | 2/2005 | Edwards et al. |
| 6,921,528 B2 | 7/2005 | Edwards et al. |
| 6,942,868 B2 | 9/2005 | Edwards et al. |
| 6,977,087 B2 | 12/2005 | Edwards et al. |
| 7,008,644 B2 | 3/2006 | Batycky et al. |
| 7,048,908 B2 | 5/2006 | Basu et al. |
| 7,052,678 B2 | 5/2006 | Vanbever et al. |
| 7,146,978 B2 | 12/2006 | Edwards et al. |
| 7,182,961 B2 | 2/2007 | Batycky et al. |
| 7,252,840 B1 | 8/2007 | Batycky et al. |
| 7,278,425 B2 | 10/2007 | Edwards et al. |
| 7,288,243 B2 | 10/2007 | Knight et al. |
| 7,384,649 B2 | 6/2008 | Batycky et al. |
| 7,435,408 B2 | 10/2008 | Edwards et al. |
| 7,469,488 B2 | 12/2008 | Chen et al. |
| 7,556,798 B2 | 7/2009 | Edwards et al. |
| 7,628,977 B2 | 12/2009 | Edwards et al. |
| 7,754,242 B2 | 7/2010 | Basu et al. |
| 7,947,742 B2 | 5/2011 | Batycky et al. |
| 7,954,491 B2 | 6/2011 | Hrkach |
| 8,053,444 B2 | 11/2011 | Reven et al. |
| 8,268,358 B2 | 9/2012 | Batycky et al. |
| RE43,711 E | 10/2012 | Jackson et al. |
| 8,404,276 B2 | 3/2013 | Jackson et al. |
| 8,415,397 B2 | 4/2013 | Batycky et al. |
| 8,454,939 B2 | 6/2013 | Hrkach |
| 8,496,002 B2 | 7/2013 | Ellwanger et al. |
| 8,545,878 B1 | 10/2013 | Kee et al. |
| 8,586,093 B2 | 11/2013 | Jackson et al. |
| 8,614,255 B2 | 12/2013 | Blizzard et al. |

(Continued)

FOREIGN PATENT DOCUMENTS

| | | |
|---|---|---|
| WO | 9703654 A2 | 2/1997 |
| WO | 9744013 A1 | 11/1997 |

(Continued)

OTHER PUBLICATIONS

Ando, K., et al., The Efficacy and Safety of Low-Dose Sirolimus for Treatment of Lymphangioleiomyomatoisis, Respiratory Investigation, vol. 51, pp. 175-183 (2013).

Aparicio, G., et al., Comprehensive Lung Injury Pathology Induced by mTOR Inhibitors, Clin. Transl. Oncol., vol. 11, pp. 499-510 (2009).

Bissler, J., et al., "Sirolimus for Angiomyolipoma in Tuberous Sclerosis Complex or Lymphangioleiomyomatosis," The New England Journal of Medicine, vol. 358, pp. 140-151 (2008).

Chhajed, P.N., et al., "Patterns of Pulmonary Complications Associated with Sirolimus," Respiration, vol. 73, pp. 367-374 (2006).

Chougule, M., et al., "Nano-liposomal Dry Powder Inhaler of Tacrolimus: Preparation, Characterization, and Pulmonary Pharmacokinetics," International Journal of Nanomedicine, vol. 2(4): pp. 675-688 (2007).

Crowe, A., et al., "Absorption and Intestinal Metabolism of SDZ-RAD and Rapamycin in Rats,"Drug Metabolism and Disposition, vol. 27(5): pp. 627-632 (1999).

(Continued)

*Primary Examiner* — Brian J Davis (74) *Attorney, Agent, or Firm* — Elmore Patent Law Group, P.C.; Darlene A. Vanstone; Carolyn S. Elmore (57) ABSTRACT

The invention provides stable, spray-dried, particle formulations containing rapamycin, or pharmaceutically acceptable salts of rapamycin, which are useful for pulmonary administration to the respiratory tract of a patient for the treatment of disease.

6 Claims, 5 Drawing Sheets

(56) References Cited

U.S. PATENT DOCUMENTS

| | | | |
|---|---|---|---|
| 8,628,754 | B2 | 1/2014 | Edwards et al. |
| 8,747,813 | B2 | 6/2014 | Batycky et al. |
| 8,887,715 | B2 | 11/2014 | Hrkach |
| 9,155,699 | B2 | 10/2015 | Jackson et al. |
| 9,333,174 | B2 | 5/2016 | Batycky et al. |
| 2003/0059375 | A1 | 3/2003 | Perez-Soler et al. |
| 2004/0018228 | A1 | 1/2004 | Fischell |
| 2004/0039047 | A1 | 2/2004 | Zamoyski |
| 2005/0119330 | A1 | 6/2005 | Kao et al. |
| 2006/0210638 | A1 | 9/2006 | Liversidge |
| 2007/0142422 | A1 | 6/2007 | Rubino et al. |
| 2008/0008662 | A1 | 1/2008 | Knight et al. |
| 2008/0063722 | A1 | 3/2008 | Ward et al. |
| 2010/0305150 | A1 | 12/2010 | Berg et al. |
| 2012/0076838 | A1* | 3/2012 | Kim ............... A61K 9/1635 424/400 |
| 2013/0004436 | A1 | 1/2013 | Lehrer |
| 2013/0102569 | A1 | 4/2013 | Blagosklonny |
| 2013/0203717 | A1 | 8/2013 | Gil et al. |
| 2014/0007874 | A1 | 1/2014 | Ellwanger et al. |
| 2014/0175686 | A1* | 6/2014 | Kim ............... A61K 9/1635 264/12 |
| 2014/0178476 | A1 | 6/2014 | Edwards et al. |
| 2015/0094378 | A1 | 4/2015 | Batycky et al. |
| 2015/0114392 | A1 | 4/2015 | Hrkach |
| 2016/0058727 | A1 | 3/2016 | Jackson et al. |

FOREIGN PATENT DOCUMENTS

| | | | |
|---|---|---|---|
| WO | 9831346 | A1 | 7/1998 |
| WO | 0113893 | A2 | 3/2001 |
| WO | 0195874 | A2 | 12/2001 |
| WO | 0285326 | A2 | 4/2002 |
| WO | 0253190 | A2 | 7/2002 |
| WO | 02083220 | A2 | 10/2002 |
| WO | 03043585 | A2 | 5/2003 |
| WO | 03043586 | A2 | 5/2003 |
| WO | 03079885 | A2 | 10/2003 |
| WO | 03079992 | A2 | 10/2003 |
| WO | 03080163 | A1 | 10/2003 |
| WO | 2004002551 | A2 | 1/2004 |
| WO | 2004112702 | A2 | 12/2004 |
| WO | 2006023627 | A1 | 3/2006 |
| WO | 2006039237 | A1 | 4/2006 |
| WO | 2006094507 | A1 | 9/2006 |
| WO | 2007088034 | A2 | 8/2007 |
| WO | 2008063581 | A2 | 5/2008 |
| WO | 2008137148 | A2 | 11/2008 |
| WO | 2008156586 | A2 | 12/2008 |
| WO | 2009026434 | A1 | 2/2009 |
| WO | 2010130982 | A2 | 11/2010 |
| WO | 2011163600 | A2 | 12/2011 |
| WO | 2015054280 | A1 | 4/2015 |
| WO | WO 2015/154084 | A1 * | 10/2015 ............... A61K 9/72 |

OTHER PUBLICATIONS

Davies, D.M., et al., "Sirolimus Therapy for Angiomyolipoma in Tuberous Sclerosis and Sporadic Lymphangioleiomyomatosis," A Phase 2 Trial, Clin. Cancer Res., vol. 17(12): pp. 4071-4081 (2011).

Hammes, S.R., et al., "Targeted Approaches Toward Understanding and Treating Pulmonary Lymphangioleiomyomatosis (LAM)," Horm. Cancer, vol. 4(2): pp. 70-77 (2013).

Hashemi-Sadraei, N., et al., "Sirolimus-Associated Diffuse Alveolar Hemorrhage in a Renal Transplant Recipient on Long-Term Anticoagulation," Clinical Nephrology. vol. 68, pp. 238-244 (2007) (Abstract Only).

Iacovelli, R., et al., "Incidence and Risk of Pulmonary Toxicity in Patients Treated with mTOR Inhibitors for Malignancy. A meta-analysis of published trials," Acta Oncologica, vol. 51, pp. 873-879 (2012).

Johnson, S.R., et al., "Survival and Disease Progression in UK Patients with Lymphangioleiomyomatosis," Thorax, vol. 59, pp. 800-803 (2004).

McCormack, F., et al., "Efficacy and Safety of Sirolimus in Lymphangioleiomyomatosis," The New England Journal of Medicine, vol. 364(17); pp. 1595-1606 (2011).

Napoli, K., et al., "Distribution of Sirolimus in Rat Tissue," Clinical Biochemistry, vol. 30(2): pp. 135-142 (1997).

Neurohr, C., et al., "Is Sirolimus a Therapeutic Option for Patients with Progressive Pulmonary Lymphangioleiomyomatosis?" Respiratory Research, vol. 12(66), 7 pages. (2011).

Nishimura, T., et al., "40-O(2-Hydroxyethyl)-Rapamycin Attenuates Pulmonary Arterial Hypertension and Neointimal Formation in Rats" Am. J., Respir. Crit Care Med., vol. 163: pp. 498-502 (2001).

Nocera, A., et al., "Sirolimus Therapy in Liver Transplant Patients: An Initial Experience at a Single Center," Transplantation Proceedings, vol. 40, pp. 1950-1952 (2008).

Pedroso, S.L., et al., "Pulmonary Alveolar Proteinosis—A Rare Pulmonary Toxicity of Sirolimus," Transplant International, vol. 20, pp. 291-296 (2007).

Perez, M.J., et al., "Interstitial Pneumonitis Associated with Sirolimus in Liver Transplantation: A Case Report," Transplantation Proceedings, vol. 39, pp. 3498-3499 (2007).

Rao, G.V.S., et al., "Efficacy of a Technique for Exposing the Mouse Lung to Particles Aspirated from the Pharynx," Journal of Toxicology and Environmental Health, Part. A., vol. 66, pp. 1441-1452 (2003).

Vahid, B., et al., "Pulmonary Complications of Novel Antineoplastic Agents for Solid Tumors," Chest, vol. 133, pp. 528-538 (2008).

Wu, K., et al., "Nonlinear Population Pharmacokinetics of Sirolimus in Patients with Advanced Cancer," CTP: Pharmacometrics & Systems Pharmacology, vol. 1, e17: doi: 10.1038/psp.2012.18, 6 pages. (2012).

Yanez, J.A., et al., "Pharmacometrics and Delivery of Novel Nanoformulated Peg-b-poly(epsilon-caprolactone) Micelles of Rapamycin," Cancer Chemother. Pharmacology, vol. 61(1): pp. 133-144 (2008).

Yi, D., et al., "Inhalation Adjuvant Therapy for Lung Cancer," Journal of Aerosol Medicine and Pulmonary Drug Delivery, vol. 23(4): pp. 181-187 (2010).

Gupta, A., et al., "Inhalable Particles Containing Rapamycin for Induction of Autophagy in Macrophages Infected with Mycobacterium Tuberculosis," Molecular Pharmaceutics, vol. 11, pp. 1201-1207 (2014).

Carvalho, S.R., et al., "Characterization and Pharmacokinetic Analysis of Crystalline Versus Amorphous Rapamycin Dry Powder Via Pulmonary Administration in Rats," European Journal of Pharmaceutics and Biopharmaceutics, vol. 88, pp. 136-147 (2014).

Mansour, H., et al., "Design and Physicochemical Characterization of Advanced Spray-Dried Tacrolimus Multifunctional Particles for Inhalation," Drug Design, Development and Therapy, vol. 7, pp. 59-72 (2013).

Chaubal, M.V., et al., "Conversion of Nanosuspensions into Dry Powders by Spray Drying: A Case Study," Pharmaceutical Research, vol. 25(10): pp. 2302-2338 (2008).

* cited by examiner

A   Batch # 106129 (25:65:8:2 Rapamycin:L-Leu:DPPC:NaCl)

B   Batch # 106186 (30:60:8:2 Rapamycin:Maltodextrin:DPPC:NaCl)

FIG. 1

C   Batch # 106187 (10:58:30:2 Rapamycin:Maltodextrin:L-Leu:NaCl)

D   Batch # 106188 (5:55:30:8:2 Rapamycin:Maltodextrin:L-Leu:DPPC:NaCl)

FIG. 1 cont.

E  Batch # 106189 (10:50:30:8:2 Rapamycin:Lactose:L-Leu:DPPC:NaCitrate)

F  Batch # 106190 (40:40:18:2 Rapamycin:Lactose:DPPC:NaCitrate)

RAPAMYCIN POWDERS FOR PULMONARY DELIVERY

RELATED APPLICATION

This application claims the benefit of U.S. Provisional Application No. 62/076,651, filed on Nov. 7, 2014. The entire teachings of the above application is incorporated herein by reference.

BACKGROUND OF THE INVENTION

Rapamycin (also known as sirolimus), is a macrocyclic lactone produced by *Streptomyces hygroscopicus*. The structural formula of rapamycin is shown below:

Rapamycin is known for its use as a therapeutic for immunosuppression and for treating transplantation rejection, host vs. graft disease, autoimmune diseases, and diseases of inflammation, solid tumors, fungal infections, adult T-cell leukemia/lymphomas and hyperproliferative vascular disorders. Rapamycin is also useful in the treatment of Lymphangiolciomyomatosis (LAM). LAM is a rare lung disease found primarily in women that often affects other organs including lymph nodes and kidneys.

Rapamycin is available in the form of crystalline powder and is known to be insoluble in water. It is known to a skilled person that the transformation of the crystalline form of a low solubility drug to the amorphous form can significantly increase the solubility thereof which is also true for rapamycin. However amorphous rapamycin is extremely chemically unstable and is therefore not easily formulated into any pharmaceutical dosage form. The present invention overcomes the problems described above by providing stable spray-dried, particle formulations of rapamycin for pulmonary administration to a patient.

SUMMARY OF THE INVENTION

The invention provides stable, spray-dried, particle formulations containing rapamycin, or pharmaceutically acceptable salts of rapamycin, which are useful for pulmonary administration to the respiratory tract, for inducing immunosuppression and for treating transplantation rejection, host vs. graft disease, autoimmune diseases, diseases of inflammation, solid tumors, fungal infections, adult T-cell leukemia/lymphomas, hyperproliferative vascular disorders and LAM.

DETAILED DESCRIPTION OF THE INVENTION

In one embodiment, the invention is a stable, pharmaceutical composition of rapamycin formulated for pulmonary delivery comprising spray-dried particles (also referred to herein as "powders" or "dry powders") comprising rapamycin, wherein rapamycin is present in the particles in amorphous form, crystalline form, or in a combination of both amorphous and crystalline forms.

In one embodiment, the invention is a pharmaceutical composition of rapamycin for pulmonary delivery comprising spray-dried particles containing rapamycin and having a tap density of less than about 0.075 g/cm$^3$. In one aspect of the invention, the tap density is from about 0.02 to 0.075 g/cm$^3$. In another aspect of the invention, the tap density is from about 0.02 to 0.05 g/cm$^3$. In a further aspect of the invention, the tap density is from about 0.03 to 0.06 g/cm$^3$. In one aspect of the invention, the tap density is from about 0.03 to 0.04 g/cm$^3$. In another aspect of the invention the median geometric size is about 5 μm to 30 μm, 5 μm to 10 μm, 7 μm to 15 μm, or 7 μm to 12 μm.

In one embodiment, the invention is a pharmaceutical composition for pulmonary delivery comprising particles containing a pharmaceutical agent and having a median geometric size of greater than about 5 microns (μm) and a tap density of less than about 0.075 g/cm$^3$.

In another embodiment, the invention is a method of delivering rapamycin to the pulmonary system of a patient comprising the steps of:

providing a spray-dried particle formulation of rapamycin in a compartment and an inhaler to a patient wherein said powder comprises particles of rapamycin;

dispersing the powder by breath actuation of the patient; and delivering the particles to the patient's respiratory system.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. No. 6,766,799, U.S. Pat. No. 7,278,425 and U.S. Pat. No. 8,496,002 each of which are hereby incorporated in by reference for their disclosure relating to the inhalation devices described therein. In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: Square root of $Cm_{H2O}$/Liters per minute.

In another aspect of the invention, the rapamycin powder in said compartment has a median geometric diameter of greater than about 5 μm, of about 5 μm to about 30 μm, of about 5 μm to about 15 μm, or of about 7 μm to about 12 μm. In one specific embodiment, the particles in said compartment have a median geometric diameter of 10-12 μm and the particles delivered to the patient's respiratory tract have a median geometric diameter of 8-9 μm. In another embodiment, the particles delivered to the patient's respiratory tract have a 5 to 20% smaller, 5 to 10% smaller, or 8 to 15% smaller median geometric diameter than the particles in said compartment.

In one embodiment, the invention is a pharmaceutical composition for pulmonary delivery comprising particles of rapamycin having a geometric size of greater than about 5 µm and a tap density of less than about 0.075 g/cm³.

In one embodiment, the particles comprise rapamycin, a phospholipid and a salt. In another aspect of this invention, the particles comprise rapamycin, a phospholipid, a salt, an optional amino acid, and an optional sugar.

Examples of salts suitable for use in the compositions of the invention include, but are not limited to sodium chloride (NaCl), sodium citrate, sodium lactate, and potassium chloride. Examples of phospholipids suitable for use in the compositions of the invention include, but are not limited to, dipalmitoylphosphatidylcholine (DPPC) dilauroylphosphatidylcholine (DLPC), disaturated-phosphatidylcholine (DSPC). Examples of amino acids suitable for use in the compositions of the invention include, but are not limited to, hydrophobic amino acids such as leucine, isoleucine, alanine, valine phenylalanine and glycine. Examples of sugars suitable for use in the compositions of the invention include, but are not limited to, lactose and maltodextrin.

In one embodiment, the pharmaceutical composition contains a powder comprising 5 to 50% rapamycin, 5-20% phospholipid, and 1-10% sodium chloride as measured by percent of dry solids in the powder. In one embodiment the pharmaceutical compositions have the formulations shown in Table 1.

| Rapamycin Formulations |
|---|
| 30:60:8:2 Rapamycin:Maltodextrin:DPPC:NaCl |
| 10:58:30:2 Rapamycin:Maltodextrin:L-Leu:NaCl |
| 5:55:30:8:2 Rapamycin:Maltodextrin:L-Leu:DPPC:NaCl |
| 10:50:30:8:2 Rapamycin:Lactose:L-Leu:DPPC:NaCitrate |
| 40:40:18:2 Rapamycin:Lactose:DPPC:NaCitrate |
| 5:75:18:2 Rapamycin:L-Leu:DPPC:NaCitrate |
| 25:65:8:2 Rapamycin:L-Leu:DPPC:NaCl |

In one embodiment, particles of this invention have an external surface area of greater than 10 m²/g. In another embodiment, the external surface area is greater than 15 m²/g, greater than 20 m²/g or about 10 to about 50 m²/g.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min. In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to herein as "fine particle fraction" or "FPF". The FPF corresponds to the percentage of particles that have an aerodynamic diameter of less than 5.6 µm. The fraction of powder that passed the first stage of the ACI and is deposited on the collection filter is referred to as "FPF(3.4)". This corresponds to the percentage of particles having an aerodynamic diameter of less than 3.4 µm.

The FPF fraction has been demonstrated to correlate to the fraction of the powder that is deposited in the lungs of the patient, while the FPF(3.4) has been demonstrated to correlate to the fraction of the powder that reaches the deep lung of a patient. In accordance with the invention, the FPF of the inhalable powder of the nominal dose contained in the capsule (i.e., the percentage of particles in the powder contained in the capsule that have an aerodynamic diameter of less than 5.6 µm) is about 40% or more. In one embodiment the FPF of the nominal dose of the inhalable powder contained in the capsule is about 50%, 60%, or 70%, or 80%, or 90%. In one embodiment the FPF is about 50% to about 60% of the nominal dose of the inhalable powder contained in the inhaler. In one embodiment the FPF is about 55% to about 65% of the nominal dose of the inhalable powder contained in the inhaler. In one embodiment the FPF is about 50% to about 70% of the nominal dose of the inhalable powder contained in the inhaler. In one embodiment the FPF is about 57% to about 62% of the nominal dose of the inhalable powder contained in the inhaler. In one embodiment the FPF is about 50% to about 69% of the nominal dose of the inhalable powder contained in the inhaler. In one embodiment the FPF is about 50%, 51%, 52%, 53%, 54%, 55%, 56%, 57%, 58%, 59%, 60%, 61%, 62%, 63%, 64%, or 65% of the nominal dose of the inhalable powder contained in the inhaler.

As used herein, the term "nominal powder dose" is the total amount of powder held in the capsule. As used herein, the term "nominal drug dose" is the total amount of Rapamycin contained in the nominal powder dose. The nominal powder dose is related to the nominal drug dose by the load percent of drug in the powder.

In one embodiment, the nominal powder dose is 25-50 mg by dry weight. In a further embodiment, the nominal powder dose is 25-40 mg by dry weight. In a still further embodiment, the nominal powder dose is 30-35 mg by dry weight or 32-38 mg by dry weight.

Another method for measuring the size distribution of airborne particles is the Multi-stage liquid Impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of an methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

In one embodiment, the inhalable powders of the invention have a tap density of less than about 0.075 g/cm³. For example, the particles have a tap density between 0.02 and 0.075 g/cm³, between 0.02 and 0.05 g/cm³, between 0.03 and 0.06 g/cm³, between 0.03 and 0.04 g/cm³, or less than about 0.05 g/cm³, or a tap density less than about 0.04 g/cm³, a tap density less than about 0.03 g/cm³. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga., 30093). Tap density is a standard measure of the envelope mass density.

Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

The inhalable powder of the invention has a preferred particle size, e.g., a volume median geometric diameter (VMGD) of at least about 1 micron (μm). In one embodiment, the VMGD is greater than 5 μm. In other embodiments, the VMGD is between about 5 μm and 30 μm, between about 5 μm and 10 μm, between about 7 μm and 15 μm and between about 7 μm and 12 μm. The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

The particles of the inhalable powder of the invention preferably have a "mass median aerodynamic diameter" (MMAD), also referred to herein as "aerodynamic diameter", between about 1 μm and about 5 μm or any subrange encompassed between about 1 μm and about 5 μm. For example, but not limited to, the MMAD is between about 1 μm and about 3 μm, or the MMAD is between about 3 μm and about 5 μm. In one embodiment, the MMAD is between 1.5 μm and 2.5 μm. Experimentally, aerodynamic diameter can be determined by employing a gravitational settling method, whereby the time for an ensemble of powder particles to settle a certain distance is used to infer directly the aerodynamic diameter of the particles. An indirect method for measuring the mass median aerodynamic diameter (MMAD) is the multi-stage liquid impinger (MSLI). The aerodynamic diameter, $d_{aer}$, can be calculated from the equation:

$$d_{aer} = d_g \sqrt{\rho_{tap}}$$

where $d_g$ is the geometric diameter, for example the MMGD, and $\rho$ is the powder density.

Powders for use in capsules of this invention are typically produced by spray drying.

In some cases, spray-drying can produce extremely dry particles which may have poor handling properties and may be difficult to compact into a capsule in a dense manner. A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

The inhalable powder comprising rapamycin as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics.

If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2. In a specific embodiment, the capsule size is 00.

In one specific embodiment, the capsule is a hydroxypropylmethylcellulose (HPMC) capsule. In another specific embodiment, the capsule is a hydroxypropylmethylcellulose size 00 capsule. In one specific embodiment the capsule material comprises HPMC and titanium dioxide and the capsule size is 00.

In one embodiment, a 00 capsule contains between 15 and 50 grams of rapamycin by dry weight. In another embodiment, a 00 capsule contains between 20 and 40 grams of rapamycin by dry weight. In another embodiment, a 00 capsule contains between 25 and 35 grams of rapamycin by dry weight. In another embodiment, a 00 capsule contains about 30, 31, 32, 33, 34, 35, 36, 37, 38, 39, or 40 grams of rapamycin by dry weight.

In one aspect of the invention, the powders have low electrostatic charge to enable high dispersion from the capsule.

The capsules of the invention are particularly suitable for use in a dry powder inhaler for the delivery of a dry powder composition comprising an effective amount of rapamycin to a patient in need thereof for example, for treating transplantation rejection, host vs. graft disease, autoimmune diseases, diseases of inflammation, solid tumors, fungal infections, adult T-cell leukemia/lymphomas and hyperproliferative vascular disorders and LAM.

As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated.

The present invention will be further understood by reference to the following non-limiting examples.

EXAMPLES

Example 1

1. Formulating Spray Solutions

Rapamycin and DPPC are allowed to equilibrate to room temperature for at least 30 minutes before weighing. Required amounts of water and ethanol are weighed and transferred to the aqueous and organic phase feed vessels respectively, and the stirring element in both vessels is turned on. The required amounts of Lactose, L-Leucine, Maltodextrin, Sodium chloride, and sodium citrate are weighed individually (wherever required) and added to the aqueous phase vessel and allowed to dissolve without allowing vortex formation. The required amount of DPPC (wherever required), and Rapamycin are weighed and added to the organic phase vessel and allowed to dissolve.

2. Spray Drying Initiation a. Formulations containing Maltodextrin

Spray drying is initiated by starting the drying gas flow (set to 100 kg/hr). The drying gas inlet temperature is set to 130 C. After the spray dryer outlet temperature reaches 80 C.°, the liquid skid inlet is set to allow blank solvents (aqueous flow=28 mL/min and organic flow=42 mL/min) to be atomized with the aid of nitrogen (atomizing gas flow=20 g/min) into the spray dryer and the system is allowed to cool and stabilize to an outlet temperature of 55 C.°.

b. Formulations not Containing Maltodextrin

Spray drying is initiated by starting the drying gas flow (set to 100 kg/hr). The drying gas inlet temperature is set to 110 C.°. After the spray dryer outlet temperature reaches 80 C.°, the liquid skid inlet is set to allow blank solvents (aqueous flow=10 mL/min and organic flow=60 mL/min) to be atomized with the aid of nitrogen (atomizing gas flow=20 g/min) into the spray dryer and the system is allowed to cool and stabilize to an outlet temperature of 55 C.°.

3. Spray Drying Continuation for Both Types of Formulations

Product filter pulsing is initiated and product filter purge flow is set to 15 scfh. After the system stabilizes at 55 C.°, the liquid skid inlet is switched to the feed solvents prepared above and the process is continued till the feed solvents run out. At the point when feed solvents run out, the liquid skid inlet is switched back to blank solvents which are allowed to spray for about 10 minutes. At this point, powder collected at the bottom of the product filter is transferred to its final collection vessel in a glove box maintained at an RH of 15%. After spraying the blank solvent for 10 minutes, the system is shut down by shutting down the liquid lines, atomization gas, drying gas heater, drying gas inlet and finally the exhaust.

4. Summary of Process Parameters

| Process Parameters | Maltodextrin formulations | non-Maltodextrin formulations |
| --- | --- | --- |
| Inlet Temperature (° C.) | 130.0 | 110.0 |
| Outlet Temperature (° C.) | 55.0 | 55.0 |
| Drying Gas Rate (kg/hr) | 100.0 | 100.0 |
| Chamber Pressure ("wc) | −2.0 | −2.0 |
| Atomization Gas Flow Rate (g/min) | 20.0 | 20.0 |
| Aqueous Flow (mL/min) | 28.0 | 10.0 |
| Organic flow (mL/min) | 42.0 | 60.0 |
| Product Filter Purge Rate (scfh) | 15.0 | 15.0 |

5. Results

Figure 1:
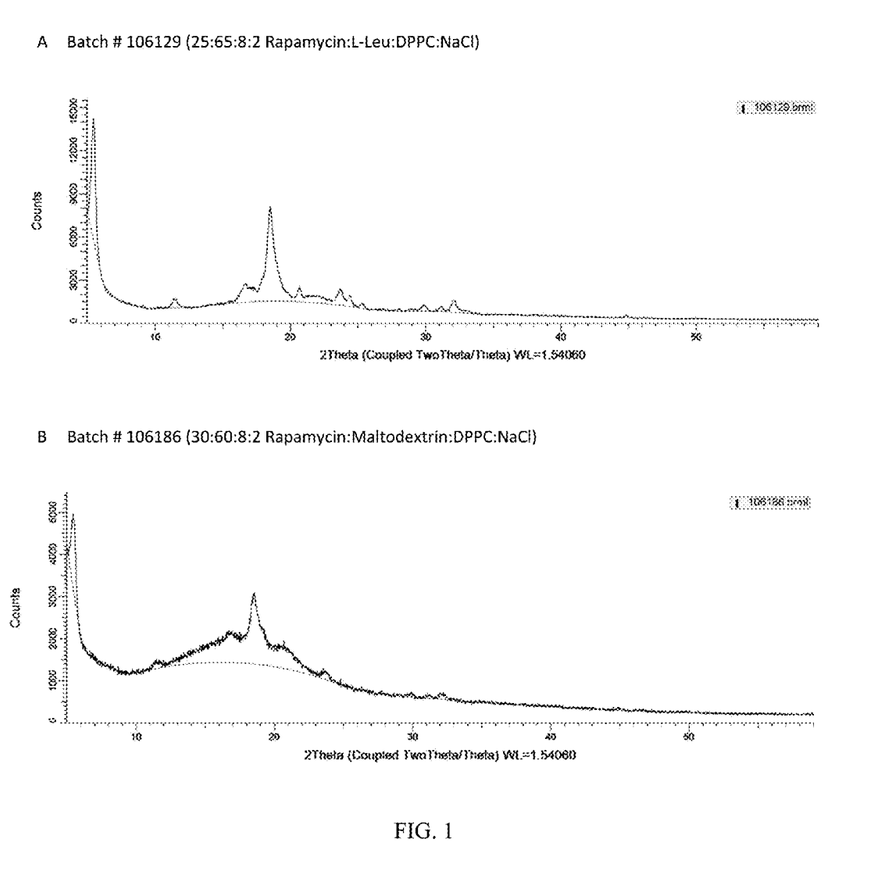
FIG. 1 shows the X-ray diffraction patterns of various lots of rapamycin spray-dried powders.
Figure 2:
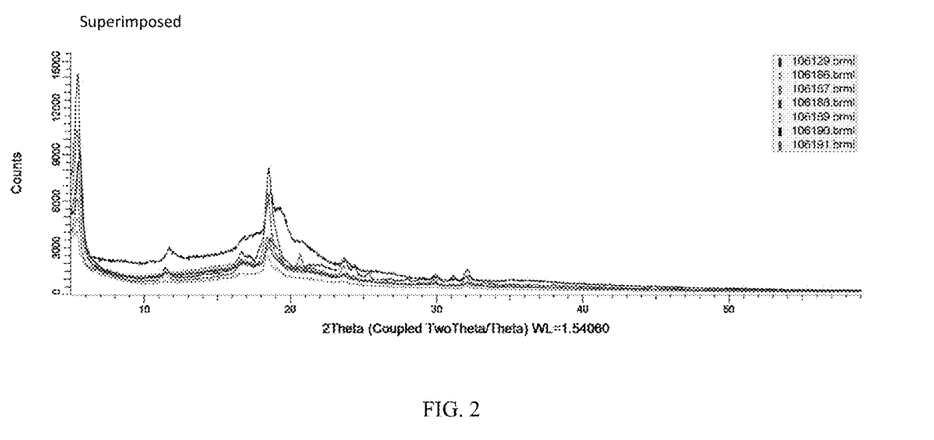
FIG. 2 shows the X-ray diffraction patterns of various lots of rapamycin spray-dried superimposed over one another.

The spray-dried formulations and their particle characteristics are shown in Table 2. The X-ray powder diffractions of the various lots are shown in FIG. 1. The same patterns as shown in FIG. 1 are superimposed on one another in FIG. 2.

TABLE 2

| Lot | Description | gPSD, D50 (um) | FPF, <5.6 um (%) | ρBulk (g/cc) | ρTap (g/cc) |
| --- | --- | --- | --- | --- | --- |
| 106186 | 30:60:8:2 Rapamycin:Maltodextrin:DPPC:NaCl | 9.2 | 54 | 0.03 | 0.05 |
| 106187 | 10:58:30:2 Rapamycin:Maltodextrin:L-Leu:NaCl | 4.8 | 47 | 0.06 | 0.10 |
| 106188 | 5:55:30:8:2 Rapamycin:Maltodextrin:L-Leu:DPPC:NaCl | 16.2 | 56 | 0.02 | 0.04 |
| 106189 | 10:50:30:8:2 Rapamycin:Lactose:L-Leu:DPPC:NaCitrate | 6.6 | 52 | 0.05 | 0.09 |
| 106190 | 40:40:18:2 Rapamycin:Lactose:DPPC:NaCitrate | 8.8 | 34 | 0.05 | 0.09 |
| 106191 | 5:75:18:2 Rapamycin:L-Leu:DPPC:NaCitrate | 6.1 | 51 | 0.08 | 0.12 |
| 106129 | 25:65:8:2 Rapamycin:L-Leu:DPPC:NaCl | 4.2 | 44 | 0.09 | 0.19 |

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

The invention claimed is:

1. A pharmaceutical composition for pulmonary delivery to the respiratory tract of a patient comprising, spray-dried particles of rapamycin and a pharmaceutically acceptable excipient.

2. The pharmaceutical composition of claim 1, wherein the pharmaceutical excipient comprises one or more of: a phospholipid, a salt, an amino acid or a sugar.

3. The pharmaceutical composition of claim 1, wherein particles comprise rapamycin in amorphous form.

4. The pharmaceutical composition of claim 1, wherein the particles comprise rapamycin in crystalline form.

5. The pharmaceutical composition of claim 1, wherein the particles comprise rapamycin in both crystalline and amorphous forms.

6. A method of delivering rapamycin to the pulmonary system of a patient comprising the steps of:

a) providing a spray-dried particle formulation of claim 1 in a compartment and an inhaler to a patient wherein said powder comprises particles of rapamycin;

b) dispersing the powder by breath actuation of the patient; and c) delivering the particles to the patient's respiratory system.

* * * * *